(12) United States Patent
Chiou et al.

(10) Patent No.: US 10,219,993 B2
(45) Date of Patent: *Mar. 5, 2019

(54) SYSTEMS AND METHODS FOR IMPROVING THE APPEARANCE OF THE SKIN

(71) Applicant: L'OREAL, Paris (FR)

(72) Inventors: Catherine Chiou, Saddle Brook, NJ (US); Angelike A. Galdi, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/391,219

(22) Filed: Dec. 27, 2016

(65) Prior Publication Data

US 2017/0189320 A1    Jul. 6, 2017

Related U.S. Application Data (63) Continuation of application No. 14/985,582, filed on Dec. 31, 2015, and a continuation of application No. 14/985,616, filed on Dec. 31, 2015.

(60) Provisional application No. 62/274,078, filed on Dec. 31, 2015.

(51) Int. Cl.
| | | |
|---|---|---|
| A61K 8/81 | (2006.01) |
| A61K 8/26 | (2006.01) |
| A61Q 19/08 | (2006.01) |
| A61K 8/58 | (2006.01) |
| A61K 8/25 | (2006.01) |
| A61Q 1/02 | (2006.01) |
| A61K 8/87 | (2006.01) |
| A61K 8/73 | (2006.01) |
| A61K 8/898 | (2006.01) |

(52) U.S. Cl.
CPC ............... *A61K 8/898* (2013.01); *A61K 8/25* (2013.01); *A61K 8/26* (2013.01); *A61K 8/585* (2013.01); *A61K 8/73* (2013.01); *A61K 8/8152* (2013.01); *A61K 8/8182* (2013.01); *A61K 8/87* (2013.01); *A61Q 1/02* (2013.01); *A61Q 19/08* (2013.01)

(58) Field of Classification Search
None
See application file for complete search history.

(56) References Cited

U.S. PATENT DOCUMENTS

| | | | | |
|---|---|---|---|---|
| 2004/0170586 A1* | 9/2004 | Ferrari | ........... | A61K 8/31 424/63 |
| 2011/0300196 A1* | 12/2011 | Mohammadi | ........ | A45D 44/002 424/401 |
| 2013/0195783 A1* | 8/2013 | Breyfogle | ........... | A61K 8/25 424/62 |

FOREIGN PATENT DOCUMENTS

| | | | | |
|---|---|---|---|---|
| EP | 2221045 A1 * | 8/2010 | ........... | A61K 8/8147 |
| WO | WO-2013078550 A1 * | 6/2013 | ........... | A61K 31/732 |

* cited by examiner

*Primary Examiner* — Monica A Shin
(74) *Attorney, Agent, or Firm* — Polsinelli PC (57) ABSTRACT

The invention relates to systems and methods for improving the appearance of the skin. The systems comprise 1) a skin-tightening composition comprising (a) at least one film former; (b) at least one polyvalent silicate thickener; (c) at least one anionic associative polymeric thickener; (d) at least one plasticizer; and (e) optionally, at least one cosmetic powder, and 2) a long-wear cosmetic composition comprising at least one silicone-polyamide copolymer, at least one silicone film former, and at least one volatile oil. Methods comprise applying the compositions of the systems on to the skin sequentially after a drying period.

13 Claims, 3 Drawing Sheets

SYSTEMS AND METHODS FOR IMPROVING THE APPEARANCE OF THE SKIN

This application claims priority to U.S. Provisional Patent Application No. 62/274,078, filed on Dec. 31, 2015, and U.S. patent application Ser. Nos. 14/985,582 and 14/985,616, filed on Dec. 31, 2015.

TECHNICAL FIELD

The disclosure relates systems containing a skin-tightening film and a long-wear cosmetic composition, and the use thereof for improving the appearance of the skin.

BACKGROUND

Many cosmetic compositions, including pigmented cosmetics such as foundations, concealers, lipsticks, mascaras, and other cosmetic and sunscreen compositions have been developed for longer wear and transfer resistance properties. This is accomplished by the use of compositions that form a film after application. Such compositions generally contain volatile solvents, which evaporate on contact with the skin or other keratinous tissue, leaving behind a layer comprising waxes and/or resins, pigments, fillers, and actives. However, these compositions tend to be uncomfortable for the wearer as the composition remains on the skin or other keratinous tissue as a brittle or non-flexible film. Such compositions may not be pliable or soft, and they may not be comfortable to wear. There may also be a tendency for such compositions to flake off because of poor adherence to the skin or other keratinous tissue. Furthermore, such compositions have a tendency to be tacky, resulting in poor application, spreadability and wear characteristics The use of fatty phases based on silicone oils makes it possible to obtain cosmetic compositions with long staying power when the oils are non-volatile or relatively non-volatile, namely good staying power over time of the color (no color change and no fading), and transfer-resistant compositions when the silicone oils are volatile, namely compositions that do not deposit onto a support such as a glass, a cup, a fabric or a cigarette, when placed in contact with the film of makeup However, there remains a need for cosmetic treatment combining a skin-tightening film and a long-wear cosmetic composition to improve the appearance of the skin. As such, there is a consumer desire for topical cosmetic formulations that are effective at reducing the appearance of skin imperfections while simultaneously reducing the appearance of wrinkles.

SUMMARY

The disclosure relates to systems and methods for improving the appearance of the skin.

In various embodiments, the disclosure relates to systems comprising:
(1) a skin-tightening composition containing (a) from about 1% to about 20% by weight of at least one film former; (b) from about 0.3% to about 0.7% by weight of at least one polyvalent silicate thickener; (c) from about 0.5% to about 15% by weight of at least one anionic associative polymeric thickener; (d) from about 2% to about 15% by weight of at least one plasticizer selected from the group consisting of glycerin, propylene glycol, butylene glycol, propanediol; (e) optionally, from about 0.1% to about 10% by weight of at least one cosmetic powder; and
(2) a long-wear cosmetic composition containing at least one silicone-polyamide copolymer, at least one silicone film former, and at least one volatile oil.

In further embodiments, the disclosure relates to methods for improving the appearance of the skin, said methods comprising applying to the skin a system comprising:
(1) a skin-tightening composition containing (a) from about 1% to about 20% by weight of at least one film former; (b) from about 0.3% to about 0.7% by weight of at least one polyvalent silicate thickener; (c) from about 0.5% to about 15% by weight of at least one anionic associative polymeric thickener; (d) from about 2% to about 15% by weight of at least one plasticizer selected from the group consisting of glycerin, propylene glycol, butylene glycol, propanediol; (e) optionally, from about 0.1% to about 10% by weight of at least one cosmetic powder; and
(2) a long-wear cosmetic composition comprising at least one silicone-polyamide copolymer, at least one silicone film former, and at least one volatile oil.

DESCRIPTIONS OF THE DRAWINGS

Implementation of the present technology will now be described, by way of example only, with reference to the attached figures, wherein.

It should be understood that the various aspects provided by the figures are not limited to the arrangements and instrumentality shown in the figures.

DETAILED DESCRIPTION

In various embodiments, the disclosure relates to systems and methods for improving the appearance of the skin. According to various embodiments, the systems according to the disclosure comprise a skin-tightening composition capable of forming a film on the skin, and a long-wear cosmetic composition, and methods comprising applying the skin-tightening composition onto the skin before or after applying the long-wear cosmetic composition onto the skin.

The systems and methods may be effective at reducing the appearance of skin imperfections. In various embodiments, the systems and methods may improve the appearance of wrinkles in the skin by forming a film on the skin that has a Young Modulus greater than that of skin, and thus has the capability of tightening the skin, while reducing the appearance of skin imperfections such as pimples, scars, age-spots, uneven skin tone, and the like, for example by blurring or hiding such skin imperfections.

As used herein, "Long-wear" compositions refer to compositions where at least one property chosen from consistency, texture, and color remains the same as at the time of application, as viewed by the naked eye, after an extended period of time, such as, for example, 1 hour, 2 hours, and further such as 8 hours. Long-wear properties may be evaluated by any method known in the art for evaluating such properties. For example, long-wear may be evaluated by a test involving the application of a composition to human skin (including lips) and evaluating the consistency, texture and color of the composition after an extended period of time. For example, the consistency, texture and color of a lip composition may be evaluated immediately following application and these characteristics may then be re-evaluated and compared after an individual has worn the lip composition for a certain amount of time. Further, these characteristics may be evaluated with respect to other compositions, such as commercially available compositions.

"Film former" or "film forming agent" as used herein means a polymer that, after dissolution in at least one solvent (such as, for example, water and organic solvents), leaves a film on the substrate to which it is applied, for example, once the at least one solvent evaporates, absorbs and/or dissipates on the substrate.

The term "long-lasting" means that the film lasts for at least about 6 hours, such as at least about 12 hours, at least about 24 hours, at least about 48 hours, or at least about 72 hours, after the film is formed on the skin.

As used herein, the term "lasting" it is meant to convey that the film is substantially intact in place on the skin.

As used herein, the term "forms quickly" with reference to a skin-tightening film means that the film forms within less than about 20 minutes, such as less than about 15 minutes, or less than about 10 minutes, after the skin-tightening composition is applied to the skin.

As used herein, the term "blur" with regard to skin imperfections means that the visual appearance of the imperfection is less noticeable.

As used herein, the term "tighten" means that the film contracts in a manner that skin has a tighter feel to the user, and that reduces the visual appearance of wrinkles in the skin.

As used herein, the term "soft focus" means that the visual appearance of the skin is more homogenous and matte, leading to the blurring or hiding of skin imperfections.

As used herein, "durable" means the film will not easily rub off, or will not be removed by sweat, water, makeup, lotions, or the like, such that the film will remain substantially intact until removed by the user.

Systems

The systems according to embodiments of the disclosure comprise a long-wear cosmetic composition and a skin-tightening composition capable of forming a film on the skin.

Long-Wear Cosmetic Composition

According to various embodiments, the long-wear cosmetic composition useful in the systems and methods described herein may be chosen from make-up, foundation, and concealer formulations. In various embodiments, the formulations may be chosen from liquid, cream, gel, mousse, stick, solid, and powder formulations.

The long-wear cosmetic composition contains at least one silicone-polyamide copolymer, at least one silicone film former, and at least one volatile oil. In at least some embodiments, the cosmetic compositions are free or substantially free of non-volatile solvent.

The long-wear cosmetic composition of this invention is described in U.S. Pat. No. 7,879,316, which is incorporated herein by reference.

Silicone-polyamide copolymers useful herein include dimethicone copolymers and dimethicone crosspolymers, preferably, a nylon-611/dimethicone copolymer. Silicone-polyamide copolymers are described in U.S. Pat. Nos. 6,451,295, 6,353,076 and 6,051,216, all of which are incorporated herein by reference.

The amount of silicone-polyamide copolymer used in the invention composition is not particularly limited, and may range from, for example, 0.1-25% by weight and more based on total weight of the composition, preferably 0.5-10% including 2, 3, 4, 5, 6, 7, 8, and 9% and all values and subranges there between. The amount of copolymer may be varied depending upon the form of the invention composition desired which, in view of this disclosure, is within the skill of the ordinary artisan.

The silicone film former of the long-wear cosmetic composition can be chosen from silsesquioxane, polyalkylsilsesquioxane, polymethylsilsesquioxane, siloxysilicate, trialkylsiloxysilicate, and trimethylsiloxysilicate.

The silicone film former may be a polymethylsilsesquioxane film former such as Belsil PMS MK, also referred to as Resin MK, available from Wacker Chemie. The weight-average molecular weight of this polymer has been estimated to be 10,000. It is believed that the polymers are in a "cage" and "ladder" configuration, as exemplified in the figures below. The majority of the polymer is in the "ladder" configuration. The ethoxy groups are generally present in an amount of 4.5% by weight and the mole percent is generally 7% (silicone units). As ethoxy groups may react with water, a small and variable amount of SiOH may also be present in the polymer. Another non-limiting example of the at least one polymethylsilsesquioxane film former suitable for use in the present invention is KR-220L, which is available from SHIN-ETSU.

Other non-limiting examples of the at least one polymethylsilsesquioxane film former that may be useful in the practice of the invention include KR-242A (which is comprised of methyl T units (98%) and dimethyl D units (2%) and has Si—OH end units) and KR-251 (which is comprised of methyl T units (88%) and dimethyl D units (12%) and has Si—OH end units), both of which are available from SHIN-ETSU.

Acceptable silicone film formers are known in the art and include, but are not limited to, those disclosed in U.S. patent application publication no. 2004/0170586, the entire contents of which is hereby incorporated by reference.

Non-limiting representative examples of acceptable film formers include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM).

Suitable examples of acceptable liposoluble polymers include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer.

One type of block copolymer which may be employed in the compositions of the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer typically comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention include block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In preferred embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Acceptable film formers also include water soluble polymers such as, for example, high molecular weight cross-linked homopolymers of acrylic acid, and Acrylates/C10-30 Alkyl Acrylate Crosspolymer, such as the Carbopol® and Pemulen®; anionic acrylate polymers such as Salcare® AST and cationic acrylate polymers such as Salcare® SC96; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof.

Depending on the application, the concentration of the at least one polymethylsilsesquioxane film former in the presently claimed composition may vary considerably. One of skill in the art will be able to determine routinely the amount of the at least one polymethylsilsesquioxane film former depending on the desired application.

In another embodiment, the silicone film former may be chosen from siloxysilicates. Preferably, the siloxysilicate is trimethylsiloxysilicate, which may or may not be in powder form. Trimethylsiloxysilicate (TMS) is commercially available from General Electric under the tradename SR1000 and from Wacker under the tradename TMS 803. TMS is also commercially available from Dow Chemical in a solvent, such as for example, cyclomethicone. However, according to the present invention, TMS may be used in the form of 100% active material, that is, not in a solvent.

Further non-limiting examples of the silicone film formers include silicone/(meth)acrylate copolymers, such as those as described in U.S. Pat. Nos. 5,061,481, 5,219,560, and 5,262,087, the disclosures of which are hereby incorporated by reference. Still further non-limiting examples of silicone film formers are non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Other non-limiting examples of silicone film formers suitable for use in the present invention are silicone esters comprising units of formulae (XIV) and (XV), disclosed in U.S. Pat. Nos. 6,045,782, 5,334,737, and 4,725,658, the disclosures of which are hereby incorporated by reference.

According to preferred embodiments, the silicone film former is present in the composition in an amount ranging from 0.1% to 30% by weight relative to the total weight of the composition. Preferably, the silicone film former is present in an amount ranging from 0.5% to 20% by weight relative to the total weight of the composition, and more preferably from 1% to 10%. One of ordinary skill in the art will recognize that the silicone film former of the present invention may be commercially available, and may come from suppliers in the form of a dilute solution. The amounts of the silicone film former disclosed herein therefore reflect the weight percent of active material.

Colorants

The long-wear cosmetic composition may further comprise a colorant component. In various embodiments, the colorant component comprises organic pigments. In further embodiments, the colorant component consists essentially of organic pigments. In yet further embodiments, the colorant component consists of organic pigments.

The organic pigments may be present in the cosmetic composition in an amount ranging from about 2% to about 90%, such as about 5% to about 80%, by weight, relative to the cosmetic composition. In embodiments where there is no, or substantially no, solvent in the cosmetic composition, the amount of organic pigment may be higher. For example, the total amount of organic pigments may be about 50% to about 90% by weight, relative to the cosmetic composition. In embodiments where the cosmetic composition comprises one or more solvents, the amount of organic pigment may be lower. For example, the total amount of organic pigments may be about 10% to about 20% by weight, relative to the cosmetic composition.

By way of non-limiting example only, organic pigments that may be used include nitroso, nitro, azo, xanthene, pyrene, quinoline, anthraquinone, triphenylmethane, fluorane, phthalocyanin, metal complex, isoindolinone, isoindoline, quinacridone, perinone, perylene, diketopyrrolopyrrole, indigo, thioindigo, dioxazine, triphenylmethane and quinophthalone compounds. For example, the organic pigments may be chosen from carmine lake, carbon black, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

Solvents

The long-wear cosmetic composition according to the present invention also comprises at least one volatile oil, preferably a silicone volatile oil, a hydrocarbon volatile oil, or a mixture thereof.

In various embodiments, the long-wear cosmetic compositions comprise at least one volatile oil, and optionally a non-volatile oil. The cosmetic compositions may, in at least certain embodiments, comprise volatile and non-volatile oils.

According to the invention, when volatile oils are present, these volatile oils permit an easier application of the composition on the skin, lips or keratinous fibers.

According to one embodiment, the composition may contain one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94.degree. C. Preferably, the volatile silicone oils have a flash point of at least 40° C.

Examples of other silicone oils that may be used in the invention include non-volatile linear polydimethylsiloxanes (PDMSs), that are liquid at room temperature; polydimethylsiloxanes comprising alkyl, alkoxy or phenyl groups, which are pendent and/or at the end of a silicone chain, these groups each containing from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

Further, a volatile linear silicone oil may be employed in the compositions of the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

The volatility of the solvents/oils can be determined using the evaporation speed as set forth in U.S. Pat. No. 6,338,839.

According to other preferred embodiments, the composition may contain one or more non-silicone volatile oils and may be selected from volatile hydrocarbon oils, alcohols, volatile esters and volatile ethers. Examples of such volatile non-silicone oils include, but are not limited to, volatile hydrocarbon oils having from 8 to 16 carbon atoms and their mixtures and in particular branched 8 to 16 carbon-atom alkanes, such as isoalkanes (also known as isoparaffins), isododecane, isodecane, isohexadecane, and for example, the oils sold under the trade names of Isopar or Permethyl. Preferably, the volatile non-silicone oils have a flash point of at least 40° C.

When present, the total amount of volatile oil may be present in the cosmetic composition in an amount ranging from about 10% to about 40%, such as from about 15% to about 30%, by weight, relative to the cosmetic composition. When present, the volatile solvent may be present in the cosmetic composition in an amount ranging from about 10% to about 30%, such as from about 15% to about 25%, by weight, relative to the cosmetic composition.

Non-volatile oils may also be present in the long-wear cosmetic composition. According to the disclosure, they include but are not limited to polar oils such as hydrocarbon-based oils of animal origin, for example perhydrosqualene; hydrocarbon-based plant oils such as liquid triglycerides of fatty acids and of glycerol, in which the fatty acids may have varied chain lengths, these chains being linear or branched, and saturated or unsaturated, which can be chosen, example, from wheatgerm oil, sunflower oil, corn oil, soybean oil, marrow oil, grapeseed oil, blackcurrant seed oil, sesame oil, hazelnut oil, apricot oil, macadamia oil, castor oil, avocado oil, karite butter, sweet almond oil, cotton oil, alfalfa oil, poppy oil, pumpkin oil, evening primrose oil, millet oil, barley oil, quinoa oil, olive oil, rye oil, safflower oil, candlenut oil, passion flower oil, musk rose oil and caprylic/capric acid triglycerides such as those sold by the company Stearineries Dubois or those sold under the names Miglyol 810, 812 and 818 by the company Dynamit Nobel; natural or synthetic esters of formula $R^1COOR^2$, wherein $R^1$ is a higher fatty acid residue comprising 7 to 19 carbon atoms, and $R^2$ is a branched hydrocarbon-based chain comprising 3 to 20 carbon atoms, such as, for example, purcellin oil (cetostearyl octanoate), isopropyl myristate and alkyl or polyalkyl octanoates, decanoates or ricinoleates; synthetic ethers of formula $R^3COR^4$, wherein $R^3$ is a $C_3$ to $C_{10}$ alkyl radical, and $R^4$ is a $C_3$ to $C_{20}$ alkyl radical; fatty alcohols comprising at least 12 carbon atoms, such as octyldodecanol or oleyl alcohol; cyclic hydrocarbons such as (alkyl)cycloalkanes, wherein the alkyl chain is linear or branched, saturated or unsaturated and comprises 1 to 30 carbon atoms, such as cyclohexane or dioctylcyclohexane; aromatic hydrocarbons, for example, alkenes such as benzene, toluene, 2,4-dimethyl-3-cyclohexene, dipentene, p-cymene, naphthalene or anthracene, and esters such as isostearyl benzoate; primary, secondary or tertiary amines such as triethanolamine; and mixtures thereof.

Additional Film Formers

In various embodiments, the long-wear cosmetic compositions may further comprise one or more additional film formers.

Without intending to be limiting, film formers may be chosen from any film forming polymer or resin capable, by itself or in the presence of an auxiliary film-forming agent, of forming a film that adheres to a support and especially to the skin. Among the film-forming polymers that may be used, mention may be made of synthetic polymers, of free-radical type or of polycondensate type, polymers of natural origin and mixtures thereof, such as acrylic polymers, polyurethanes, polyesters, polyamides, polyureas, cellulose-based polymers, for instance nitrocellulose, and latex film forming polymers. For example, latex film forming polymers may be chosen from acrylate latex polymers, polyurethane latex polymers, and mixtures thereof. As still further examples of film forming polymers, latex film forming polymers may be chosen from at least one random styrene acrylate copolymer or derivative thereof, and at least one acrylate copolymer or derivative thereof, and mixtures thereof. Further, resinous plant extracts such as rosin and shellac, or derivatives thereof, epoxy ester resins, polyvinylpyrrolidone (PVP), polyvinylpyrrolidone/vinyl acetate copolymers and vinyl acetate/crotonic acid copolymers, and silicone resins may also be mentioned By way of examples, suitable film forming polymers and resins include sulfopolyester resins, such as AQ sulfopolyester resins, for example AQ29D, AQ35S, AQ38D, AQ38S, AQ48S, and AQ55S (available from Eastman Chemicals), Vinex resins, such as Vinex 2034, Vinex 2144, and Vinex 2019 (available from Air Products), Dermacryl acrylic resins (available from National Starch), polyvinylpyrrolidinones (PVP) such as Luviskol K17, K30, and K90 (available from BASF), water soluble copolymers of PVP, including PVP/VA S-630 and W-735 and PVP/dimethylaminoethylmethacrylate, and Copolymers such as Copolymer 845 and Copolymer 937 available from ISP.

The film former may be present in the cosmetic composition in an amount ranging from about 1% to about 20%, such as from about 5% to about 15%, by weight, relative to the cosmetic composition.

The long-wear cosmetic composition may further comprise any component traditionally used in compositions for making up the skin, including but not limited to surfactants, co-solvents (volatile and/or non-volatile), waxes, plasticizers, preservatives, fillers, active ingredients used to treat skin, and sunscreens. Of course, the skilled artisan will take care to choose components that do not, or do not substantially, negatively affect the skin-tightening properties of the film produced by the skin-tightening compositions of the systems and methods described herein.

Skin-Tightening Compositions

According to various embodiments, the skin-tightening compositions useful in the systems and methods described herein comprise: (a) at least one film former; (b) at least one polyvalent silicate thickener; (c) at least one anionic associative polymeric thickener; (d) at least one plasticizer; and (e) optionally, at least one cosmetic powder.

For example, the composition s may comprise: from about 1% to about 20% by weight of at least one film former; from about 0.3% to about 0.7% by weight of at least one polyvalent silicate thickener; from about 0.5% to about 15% by weight of at least one anionic associative polymeric thickener; from about 2% to about 15% by weight of at least one plasticizer; and optionally, from about 0.1% to about 10% by weight of at least one cosmetic powder.

Upon application to the skin, the compositions provide an immediate tightening sensation and reduce skin imperfections. The compositions can have an alkaline pH. For example, in some cases, the pH value may be in the range of 10 to 12, 10.5 to 11.5, or 11 to 11.5.

The at least one film former may be, for example, sodium silicate, colloidal silica, pullulan, polycacrylate-21 (and) acrylates/dimethylaminoethylmethacrylate copolymer, polyurethanes, polysaccharides, polyvinylpyrrolidone, polyacrylates, acrylate copolymers, and the mixtures thereof. In some cases, the at least one film former comprises a polysaccharide, which may have one or more free hydroxyl groups. Furthermore, in some cases, the polysaccharide is pullulan. In some cases, the composition comprises at least two film formers, which may be any two film formers, e.g., sodium silicate and pullulan. Typically, the at least one film former is present in an amount from 1% to 20%, 1% to 18%, 1% to 16%, 1% to 14%, 1% to 12%, 1% to 10%, 1% to 8%, 2% to 20%, 2%, 18%, 2% to 16%, 2% to 16%, 2% to 14%, 2% to 12%, 2% to 10%, 2% to 8%, 3% to 20%, 3% to 18%, 3% to 16%, 3% to 14%, 3% to 12%, 3% to 10%, 3% to 8%, 4% to 20%, 4% to 18%, 4% to 16%, 4% to 14%, 4% to 14%, 4% to 12%, 4% to 10%, 4% to 8%, 5% to 20%, 5% to 18%, 5% to 16%, 5% to 14%, 5% to 12%, 5% to 10%, 5% to 8%, or 3% to 15%, by weight of the total weight of the composition.

The polyvalent silicate thickener may be selected from the group consisting of magnesium silicate, calcium silicate, aluminum silicate, a polyvalent silicate clay, montmorillonite, bentonite, smectite, and mixtures thereof. In some cases, the polyvalent silicate thickener is montmorillonite. In some cases, the polyvalent silicate thickener is organically modified clay such as kaolinite, smectite, bentonite, and/or montmorillonite The polyvalent silicate thickener is typically present in an amount of 0.1% to 0.9%, 0.1% to 0.8%, 0.1% to 0.7%, 0.2% to 0.9%, 0.2% to 0.8%, 0.2% to 0.7%, 0.3% to 0.9%, 0.3% to 0.8%, 0.3% to 0.7%, 0.4% to 0.9%%, 0.4% to 0.8%, 0.4% to 0.7%, 0.4% to 0.9%, 0.4% to 0.8%, 0.4% to 0.7%, 0.4% to 0.6%, or about 0.5%.

The compositions of the disclosure typically include at least one anionic associative polymeric thickener. The at least one anionic associative polymeric thickener may be selected from the group consisting of an acrylate copolymer, an acrylates/beheneth-25 methacrylate copolymer, an acrylates/steareth-20 methacrylate copolymer, and mixtures thereof. Furthermore, the at least one anionic associative polymeric thickener may include acrylates/steareth-20 methacrylate copolymer such as Aculyn™ 22 (Dow Chemical Company); acrylates/beneneth-25 methacrylate copolymer such as Novethix™ (Lubrizol); acrylate copolymer such as Carbopol® Aqua SF-1 Polymer (Lubrizol). The at least one anionic associative polymer thickener is typically present in an amount from 0.5% to 15%, 1% to 15%, 1% to 14%, 1% to 13%, 1% to 12%, 1% to 10%, 1% to 8%, 2% to 15%, 2% to 14%, 2% to 13%, 2% to 12%, 2% to 10%, 2% to 8%, or 2% to 6%, by weight of the total composition. Many anionic associative polymeric thickeners are water-soluble, and increase the viscosity of water or form an aqueous gel when the cosmetic compositions of the disclosure are dispersed/dissolved in water.

The compositions of the disclosure typically include at least one plasticizer. The at least one plasticizer may be, for example, propylene glycol, polyethylene glycol, glycerol, sorbitol, dipropylene glycol, glycerin, propane diol, triethyl citrate, isohexadecane, and sodium hyaluronate. Typically, the plasticizer is present in an amount of 1% to 15%, 1% to 14%, 1% to 13%, 1% to 12%, 1% to 11%, 1% to 10%, 2% to 15%, 2% to 14%, 2% to 13%, 2% to 12%, 2% to 11%, 2% to 10%, 5% to 15%, 5% to 14%, 5% to 13%, 5% to 12%, 5% to 11%, 5% to 10%, or 9% to 11% by weight of the total weight of the composition.

The compositions described herein may include at least one cosmetic powder. Cosmetic powders can be used to help formulate compositions that are smooth and soft on the skin. Representative cosmetic powders include, but are not limited to, talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polystyrene powder, silk powder, crystalline cellulose, starch, titanated mica, iron oxide titanated mica, bismuth oxychloride, and the like. Additional powders include, but are not limited to, inorganic powders, such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder, such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder, such as hydroxyethyl cellulose and sodium carboxymethyl cellulose, ethylene glycol monostearate; inorganic white pigments, such as magnesium oxide. Representative cosmetic powders include, for example, polymethylsilsesquioxane, methyl polymethacrylate crosspolymer, Nylon-12, silica and boron nitride, and combinations thereof.

In some cases, the cosmetic powder may be selected from the group consisting of talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polymethyl Methacrylate, polystyrene powder, silk powder, crystalline cellulose, and mixtures thereof. In some cases, the cosmetic powder is polymethyl methacrylate.

When present, the one or more cosmetic powders may be present in an amount of 0.1% to about 25%, 0.1% to 20%, 0.1% to 15%, 0.1% to 10%, 0.1% to 8%, 0.1% to 6%, 0.1% to 4%, 0.5% to 20%, 0.0.5% to 15%, 0.5% to 10%, 0.5% to 8%, 0.5% to 6%, 0.5% to 4%, 1% to 20%, 1% to 15%, 1% to 10%, 1% to 8%, 1% to 6%, 1% to 4%, 2% to 10%, 2% to 8%, 2% to 6%, or 3% to 7%, based on the total weight of the composition.

The instant disclosure also relates to methods for improving the appearance of skin comprising applying the compositions described herein to the skin. Furthermore, the instant disclosure relates to methods for firming and/or tightening the skin comprising applying the compositions described herein to the skin and forming a skin-tightening film or layer on the skin. In some instances, the compositions are applied to the skin of the face, and/or more specifically around the eyes, around the mouth, and/or around the neck. The methods of improving the appearance of skin include methods for treating or reducing the appearance of wrinkles, blemishes, dryness, roughness, dullness, age spots, and sagging, and/or puffy skin.

The compositions of the present disclosure may be in the form of a liquid dispersion, a gel, a cream, a lotion, a mousse, or a spray. The composition may be in the form of a liquid emulsion, such as a liquid-lotion, liquid-gel, liquid-cream, or a cream emulsion, such as a thick cream or gel-cream, foam or mousse wherein the liquid emulsion form has a thinner consistency than the cream emulsion form.

The compositions of the present disclosure are typically aqueous compositions. For example, the compositions may have 20% to 80%, 20% to 70%, 20% to 60%, 20% to 50%, 20% to 40%, 20% to 30%, 30% to 80%, 30% to 70%, 30% to 60%, 30% to 50%, 30% to 40%, 35% to 65%, or 40% to 60% water.

Skin-Tightening Film

When the skin-tightening compositions according to the disclosure are applied to the skin, the at least one thermoplastic elastomer, the at least one adhesive polymer, and the at least one filler together form a matrix that creates a film on the skin. The film formed by the compositions described herein form quickly, are long-lasting and durable, and have optical properties that are advantageous for a skin-tightening film, such as transparency, matte effect, and a soft focus effect which helps to blur skin imperfections so that they are less noticeable.

Methods

Methods of improving the appearance of the skin using the systems described herein are also disclosed, said methods comprising applying a skin-tightening composition according to the disclosure onto the skin in order to form a film on the skin, either before or after applying a long-wear cosmetic composition to the skin. Methods comprise tightening the skin, e.g. to get rid of, or reduce the appearance of, wrinkles, eye bags, etc., while also blurring or hiding skin imperfections, e.g. to camouflage pimples, pores, dark spots, uneven pigmentation, etc.

Optionally, in various methods, the skin tightening composition of the systems described herein may be applied to the skin first as a base coat, followed by an optional drying time during which a skin-tightening film is formed on the skin, followed by applying the long-wear cosmetic composition onto the skin on top of the film.

In further methods, the long-wear cosmetic composition of the systems described herein may be applied to the skin first as a base coat, followed by an optional drying time to allow the cosmetic composition to dry, and followed by applying the skin-tightening composition onto the skin on top of the cosmetic composition to form a skin-tightening film thereon.

Surprisingly and unexpectedly, the skin-tightening composition works in synergy with the long-wear cosmetic composition. The systems and methods described herein avoid or minimize the drawback of migration of pigments from the long-wear cosmetic composition. Furthermore, the association of the skin-tightening composition and the long-wear cosmetic composition avoids or minimizes the softening of the skin-tightening film, which can diminish the film's skin-tightening properties.

Further, the systems and methods described herein provides for an appearance of the skin that has a substantially homogenous coloration that is long-lasting and durable. The systems and methods thus effectively hide skin imperfections while simultaneously minimizing the appearance of wrinkles. In at least certain embodiments, the appearance of skin imperfections, wrinkles, or both may be minimized to a greater extent with the systems and methods of the disclosure, as compared to either skin-tightening compositions or long-wear cosmetic compositions alone.

Kits

The disclosure further relates to kits comprising, in one compartment, (1) a skin-tightening composition comprising (a) at least one film former; (b) at least one polyvalent silicate thickener; (c) at least one anionic associative polymeric thickener; (d) at least one plasticizer; and (e) optionally, at least one cosmetic powder; and in a second compartment (2) a long-wear cosmetic composition comprising at least one silicone-polyamide copolymer, at least one silicone film former, and at least one volatile oil.

It is to be understood that, as used herein the terms "the," "a," or "an," mean "at least one," and should not be limited to "only one" unless explicitly indicated to the contrary. Thus, for example, reference to "a portion" includes examples having two or more such portions unless the context clearly indicates otherwise.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints.

It is understood that when an amount of a component is given, it is intended to signify the amount of the active material.

It should be understood that all patents and published patent applications referenced are incorporated herein in their entireties.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

The compositions and methods according to the present disclosure can comprise, consist of, or consist essentially of the elements and limitations described herein, as well as any additional or optional ingredients, components, or limitations described herein or otherwise known in the art.

It will be apparent to those skilled in the art that various modifications and variations can be made in the delivery system, composition and methods of the invention without departing from the spirit or scope of the invention. Thus, it is intended that the present invention cover the modifications and variations of this invention provided that they come within the scope of the appended claims and their equivalents.

As used herein, all percentages are by weight (wt. %) of the total composition.

All numeric ranges are inclusive of narrower ranges; delineated upper and lower range limits are interchangeable to create further ranges not explicitly delineated. All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The foregoing description illustrates and describes the disclosure. Additionally, the disclosure shows and describes only the exemplary embodiments but, as mentioned above, it is to be understood that it is capable to use in various other combinations, modifications, and environments and is capable of changes or modifications within the scope of the disclosed concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

EXAMPLES

The following Examples are provided for illustrative purposes only, and are not intended to be limiting.

Example 1 (Formulas 1-22)

TABLE 1

| | Formula | | | | |
|---|---|---|---|---|---|
| Ingredient/US INCI Name | 1 % | 2 % | 3 % | 4 % | 5 % |
| Sodium Silicate | 3.5-5.0 | 5.5-5.8 | 6-6.8 | 7.5-8 | 8.5-9.5 |
| Polyvalent Silicate[1] | 0.50-0.70 | 0.6-0.7 | 0.3-0.5 | 0.4-0.6 | 0.6-0.7 |
| Acrylates Copolymer | 0.5-2.0 | 6-10 | 11-15 | 2-6 | 9-13 |
| Second Film Former[2] | 4.0-5.0 | 3.0-4.0 | 8-10 | 2-3 | 5-4 |
| Cosmetic Powder | 3.0 | 3.0 | 3.0 | 3.0 | 3.0 |
| Water | QS | QS | QS | QS | QS |
| Plasticizer[3] | 8-10 | 4.0-6.0 | 10-12 | 5-7 | 3-5 |

[1]Vermiculite, Montmorillonite.
[2]Polyurethanes, Polysaccharides, Polyvinylpyrrolidone, Acrylates and Colloidal Silicate.
[3]Propylene Glycol, Polyethylene Glycol, Glycerol, Sorbitol, Dipropylene Glycol, Glycerin, Propanediol, Triethyl Citrate, Isohexadecane.

TABLE 2

| | Formula | | | | | |
|---|---|---|---|---|---|---|
| Ingredient/US INCI Name | 6 % | 7 % | 8 % | 9 % | 10 % | 11 % |
| Sodium Silicate | 5 | 5.6 | 6.5 | 7.5 | 8 | 9 |
| Montmorillonite | 0.5 | 0.7 | 0.4 | 0.6 | 0.6 | 0.7 |
| Acrylates Copolymer | 3 | 7 | 13 | 4 | 12 | 11 |
| Pullulan | 5 | 4 | 9 | 2 | 5 | 4 |
| Polymethyl Methalacrylate | 3 | 4.5 | 7 | 4 | 3 | 3 |
| Water | QS | QS | QS | QS | QS | QS |
| Glycerin | 10 | 5 | 11 | 6 | 4 | 8 |

TABLE 3

| | Formula | | | | |
|---|---|---|---|---|---|
| Ingredient/US INCI Name | 12 % | 13 % | 14 % | 15 % | 16 % |
| Polyvalent Silicate[1] | 0.50-0.70 | 0.6-0.7 | 0.3-0.5 | 0.4-0.6 | 0.6-0.7 |
| Acrylates Copolymer | 8.0-12.0 | 6-10 | 11-15 | 2-6 | 9-13 |
| Film Former[2] | 4.0-5.0 | 3.0-4.0 | 8-10 | 2-3 | 5-4 |
| Cosmetic Powder | 3.0 | 3.0 | 3.0 | 3.0 | 3.0 |
| Water | QS | QS | QS | QS | QS |
| Plasticizer[3] | 8-10 | 4.0-6.0 | 10-12 | 5-7 | 3-5 |

[1]Vermiculite, Montmorillonite.
[2]Polyurethanes, Polysaccharides, Polyvinylpyrrolidone, Acrylates copolymer and Colloidal Silicate.
[3]Propylene Glycol, Polyethylene Glycol, Glycerol, Sorbitol, Dipropylene Glycol, Glycerin, Propanediol, Triethyl Citrate, Isohexadecane.

TABLE 4

| | Formula | | | | | |
|---|---|---|---|---|---|---|
| Ingredient/US INCI Name | 17 % | 18 % | 19 % | 20 % | 21 % | 22 % |
| Montmorillonite | 0.5 | 0.7 | 0.4 | 0.6 | 0.6 | 0.7 |
| Acrylates Copolymer | 3 | 7 | 13 | 4 | 12 | 11 |
| Pullulan | 5 | 4 | 9 | 2 | 5 | 4 |
| Polymethyl Methalacrylate | 3 | 4.5 | 7 | 4 | 3 | 3 |
| Water | QS | QS | QS | QS | QS | QS |
| Glycerin | 10 | 5 | 11 | 6 | 4 | 8 |

In making the formulations in the above tables, the following procedure was used. The polyvalent silicate was introduced in portions with medium sweep and shear to the main kettle containing water at room temperature and mixed for about 5 to 10 minutes, or until the ingredient was fully hydrated and the mixture was homogenous. The polysaccharide was added in portions with medium sweep and shear. Then, the cosmetic powder was added. The mixture was mixed for 5 to 10 minutes or until uniform. The glycerin was added and mixed for 5 minutes or until uniform. The homogenizer was turned off. Then, the vacuum was pulled until air bubbles were removed. The anionic associative polymeric thickener was slowly added directly to the main kettle as to not cause aeration. While still under the vacuum, continued to mix the ingredients. The sodium silicate was added slowly to neutralize the thickener, using low sweep and pull vacuum. Mixing was continued until the thickener was neutralized and the formula appeared uniform.

Example 2 (Comparative)

TABLE 5

| | Formula | | | | | | |
|---|---|---|---|---|---|---|---|
| US INCI Name | 23 % | 24 % | 25 % | 26 % | 27 % | 28 % | 29 % |
| Sodium Silicate | 5 | 5 | 5 | 5 | 5 | 5 | 5 |
| Polyvalent Silicate | 1 | 1 | 1 | 1 | 1 | 1 | 0 |
| Acrylates Copolymer | 3 | 3 | 3 | 3 | 3 | 3 | 3 |
| Pullulan | 5 | 5 | 5 | 5 | 5 | 5 | 5 |
| Polymethyl Methalacrylate | 3 | 0 | 0 | 0 | 3 | 3 | 6 |
| Silica | 0 | 5 | 5 | 0 | 0 | 0 | 0 |
| Sodium Hyaluronate | 0 | 0 | 0 | 0 | 0.25 | 0.5 | 0 |

TABLE 5-continued

| | Formula | | | | | | |
|---|---|---|---|---|---|---|---|
| US INCI Name | 23 % | 24 % | 25 % | 26 % | 27 % | 28 % | 29 % |
| Plasticizer | 10 | 0.5 | 3.2 | 3 | 10 | 10 | 10 |
| Water | QS | QS | QS | QS | QS | QS | QS |
| TOTAL (%) | 100 | 100 | 100 | 100 | 100 | 100 | 100 |

Table 5 shows various compositions which were formed using the same process as Example 1.

If the amount of polyvalent silicate was equal to 1%, like in Formulas 23-28, the compositions (the films) crack after application to the skin. If the polyvalent silicate was not present in the formula (0%), like in Formula 29, the composition was too soft and did not provide the properties of a skin tightening. When the amount of polyvalent silicate was greater than 0% but less than 1%, or about 0.5%, the composition provided an unexpectedly strong, flexible, and durable skin tightening composition.

The present application was compared to several commercially available products such as Serious Skincare Firm-A-Face XR™ All Over Skin Tightener, Peter Thomas Roth Instant FIRMx Temporary Face Tightener, Fusion Beauty Nip Line Erase Instant Line Remover, Hydroxatone 90 Second Wrinkle Reducer, NuNutrients Facelift, Renoir No Lines Temporary Wrinkle Remover and Instantly Ageless®. The commercially available products provided a tightening sensation and visual changes to the skin within 5 minutes. Nonetheless, they also presented many negative characteristics upon drying such as whitening, cracking of the film, and incompatibility with the various makeup regiments. Furthermore, the beneficial results (e.g., the skin tightening properties) were not long-lasting. The compositions of the instant disclosure were long-lasting. The compositions retained their beneficial results (e.g., the skin tightening properties) without whitening, cracking, or peelings for a much longer period of time than the commercially available products, e.g., longer than 30 min, 1 hour, 3 hours, 4 hours, 5 hours, or 6 hours.

In the section below, Formula 6 from Example 1 (Table 2) was compared with Instantly Ageless®. Instantly Ageless® contains sodium silicate, magnesium aluminum silicate, acetyl hexapeptide-3, phenoxyethanol, ethylhexylglycerin, water, Yellow 5 and Red 40.

To compare the two compositions, an instrumental evaluation, utilizing the Cutometer MPR 580 (Courage and Khazaja, Köln, Germany), was carried out. The Cutometer Study measured the skin elasticity of the eyebags. The objective of this study was to collect cutometer data to determine the relationship between skin elasticity and aesthetician grading for eyebag appearance and to correlate changes in skin elasticity and wrinkle visibility after application of film technology with changes in eyebag grade.

An expert evaluation of eye bags was also performed by an aesthetician using a 7 point scale atlas grading. The efficacy of the product was examined at T=0, 10 min, 30 min, 3 hours, and 6 hours. Women with baseline Grade 4 eye bags experience an average of 2.5 grade reduction in puffiness for 6+ hours after application of the compositions described herein.

After application of Instantly Ageless® to the skin, an immediate tightening of the skin was observed, but the tightening almost immediately began to dissipate and the product formed white film, cracked, and caused slight irritation. Instantly Ageless showed an average reduction of 1 grade with a higher tendency of film flaws such as whitening and cracking. On the contrary, the inventive compositions exhibited long-lasting results for at least 6 hours and an average of 2.5 grade reduction in eye bag puffiness.

Figure 1:
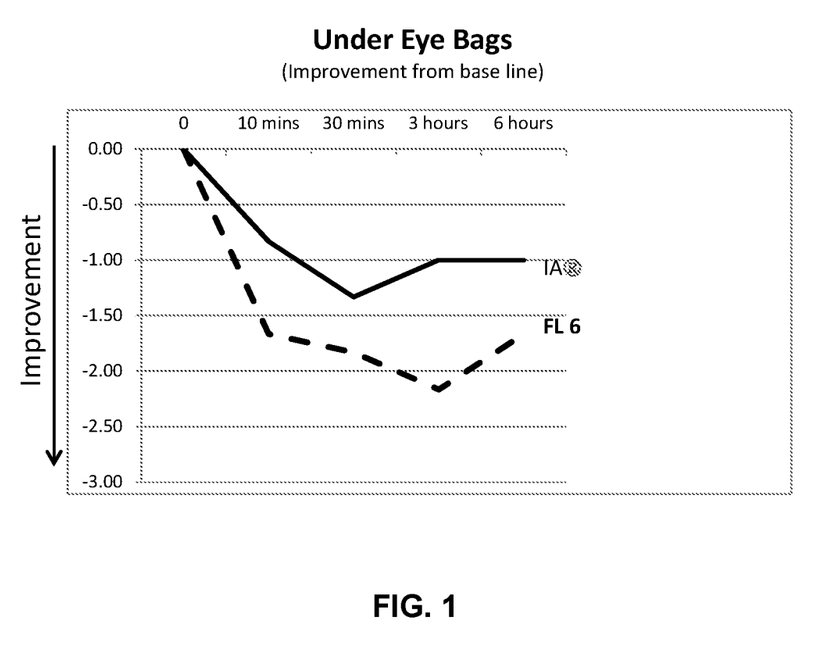
FIG. 1 is a graph comparing the results of inventive Formula 6 and the commercially available product Instant Ageless® on under eye bags. The graph illustrates time versus improvement of the under eye bags.
Figure 2:
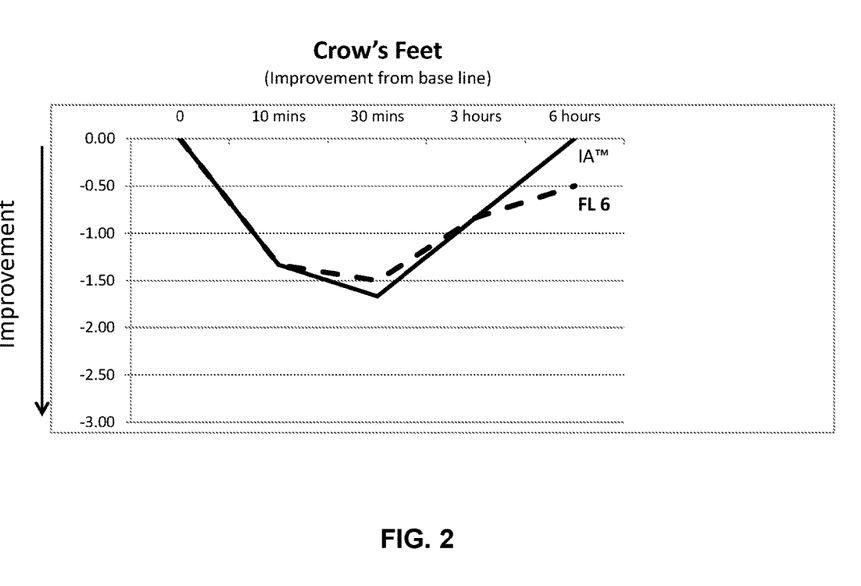
FIG. 2 is a graph comparing the results of inventive Formula 6 and the commercially available product Instant Ageless® on crow's feet. The graph illustrates time versus improvement of crow's feet.

FIGS. 1 and 2 compare the inventive example and the commercially available product Instantly Ageless®. FIG. 1 represents the reduction of under eye bags over time. The study was completed with 6 Caucasian women aged 40-60 years with Grade 4 eye bags (Aging Atlas grade).

As observed in FIG. 1, the inventive composition provided dramatic results compared to Instantly Ageless®. An instant improvement was noticeable in 10 minutes and lasted over 6 hours. On the other hand, whitening, flaking, and cracking, appeared within only 3 hours with Instantly Ageless®.

FIG. 2 represents the reduction of crow's feet. The inventive composition provided longer lasting results compare to Instantly Ageless®. The inventive composition showed only very slight film flaws after 3 hours; whereas film flaws began appearing at 30 minutes for Instantly Ageless®.

Example 3 (Film Property Tests)

Thickeners were tested according to three criteria: compatibility, viscosity, and tightening. Below is a Table of the different thickeners tested with their results.

TABLE 6

| | Thickeners | | |
|---|---|---|---|
| INCI Name | Compatibility | Viscosity | Tightening |
| Acrylates/steareth-20 methacrylate copolymer[1] | + | − | + |
| Acrylates/beneneth-25 methacrylate copolymer[2] | + | + | + |
| PVP[3] | − | + | + |
| Acrylates/C10-30 alkyl acrylate copolymer[4] | − | − | N/A |
| Acrylates/beneneth-25 methacrylate copolymer[5] | + | − | + |
| Acrylates/steareth-20 methacrylate copolymer[6] | + | − | + |
| Acrylates/C10-30 alkyl acrylate copolymer[7] | − | − | + |
| Acrylates/C10-30 alkyl acrylate copolymer[8] | − | − | + |
| Acrylate copolymer[9] | + | + | + |
| Acrylates/C10-30 alkyl acrylate copolymer[10] | + | + | − |
| Acrylates/C10-30 alkyl acrylate copolymer[11] | + | − | − |
| Montmorillonite[12] | + | + | + |

[1] Aculyn 22 Polymer, available from Dow Chemical.
[2] Novethix L-10 Polymer, available from Lubrizol.
[3] Flexithix, available from Ashland
[4] Carbopol 1382 Polymer, available from Lubrizol.
[5] Aculyn 28 Polymer, available from Lubrizol.
[6] Aculyn 88 Polymer, available from Lubrizol.
[7] Carbopol Ultrez 21 Polymer, available from Lubrizol.
[8] Carbopol Ultrez 20 Polymer, available from Lubrizol.
[9] Carbopol Aqua SF-1 Polymer, available from Lubrizol.
[10] Pemulen TR-2 Polymer, available from Lubrizol.
[11] Pemulen TR-1 Polymer, available from Lubrizol.
[12] GelWhite-H XR, available from BYK Additives & Instruments.

Table 6 shows that the acrylates/benenth-25 methacrylate copolymer, the acrylates copolymer, and the montmorillonite presented positive results (+) for all three parameters: compatibility, viscosity and tightening.

Film formers were tested according to three criteria: compatibility, formed film, and tightening. Below is a table of the different film formers tested with their respective results.

TABLE 7

Film Formers

| INCI Name | Compatibility | Formed Film | Tightening |
|---|---|---|---|
| Polyurethane-35[1] | + | − | − |
| Polyurethan-2 (and) Polymethyl methacrylate[2] | + | − | − |
| Pullulan | + | + | + |
| PVP[3] | + | + | − |
| Polycacrylate-21 (and) acrylates/dimethylaminoethylmethacrylate copolymer[4] | + | + | + |
| Polyacrylate-2 crosspolymer[5] | − | N/A | N/A |
| Polyacrylate-32[6] | + | − | − |
| AMP-acrylates/allyl methacrylate coloymer[7] | + | − | − |
| Silica[8] | + | + | + |
| Sodium Silicate | + | + | + |

[1]Baycusan C 1004, available from Bayer Material Science.
[2]Hybridur 875 Poymer Dispersion, available from Air Products.
[3]PVP K30L, available from Ashland.
[4]Syntran PC5100 CG, available from Interpolymer
[5]Fixate Superhold Polymer, available from Lubrizol
[6]Fixate Design Polymer, available from Lubrizol
[7]Fixate G100L PR Polymer, available from Lubrizol
[8]Colloidal Silica, Ludox AM X6021, available from Grace Davison.

Pullulan, polycacrylate-21 (and) acrylates/dimethylaminoethylmethacrylate copolymer, silica, and sodium silicate provided the best film-forming properties, as shown by the positive (+) results for all three properties: compatibility, formed film, and tightening.

A standard safety test for eye products, called BCOP (Bovine Corneal Opacity and Permeability), was conducted in vitro to measure the level of irritation of the products. The results showed that the inventive composition was cosmetically acceptable and caused only mild, if any, irritation.

Example 4 (pH Study with Composition Containing Sodium Silicate)

A study of the pH was performed. The results showed that if the pH was below 10, the composition became more solid. However, it was found that when the pH was in the range of 10 to 12, or 11 to 11.5, the composition exhibited special properties. For example, the composition exhibited excellent film-forming properties on the skin and the film exhibited unexpectedly long-lasting strength, durability, and flexibility (elasticity).

Example 5. Long-Wear Cosmetic Compositions

Tables 8-11 illustrate examples of long-wear cosmetic compositions.

TABLE 8

Long-Wear Foundation Composition

| Phase | INCI Name | % |
|---|---|---|
| A | Cyclopentasiloxane (and) dimethicone copolyol | 8.0 |
| | Polyglyceryl-4 isostearate (and) hexyl laurate (and) cetyl PEG/PPG-10/1 dimethicone | 3.5 |
| | Treated pigments | 9.9 |
| B1 | Cyclopentasiloxane (volatile oil) | 26.1 |
| | Polysiloxane/polyamide (PASi) | 3.0 |
| B2 | Polytrap/cyclopentasiloxane (filler) | 1.0 |
| | MMA crosspolymer (filler) | 4.0 |
| | Nylon-12 (filler) | 1.0 |
| B3 | Preservative | 0.4 |
| | Disteardimonium Hectorite | 0.6 |
| | Propylene carbonate | 0.2 |
| C | Water | 40.0 |
| | Magnesium sulfate | 1.0 |
| | Preservatives | 0.7 |
| | Non-ionic emulsifier | 0.5 |
| | Total | 100.0 |

The foundation is obtained by heating phase B1 until softening of this phase; adding phase B2 with stirring, then phase B3; adding phase A at a temperature 20° C. below the preceding temperature, then adding phase C under stirring.

The product obtained in this way has, because of the incorporation into the liquid fatty phase of a polysiloxane (PS) polyamide (PA) polymer, according to the invention, excellent non-transfer properties (demonstrated by the non-deposition of foundation on a small collar placed around the neck of made-up testers for several minutes).

TABLE 8

Long-Wear Foundation Composition

| Phase | INCI Name | % |
|---|---|---|
| A | Cyclopentasiloxane (and) dimethicone copolyol | 8.0 |
| | Polyglyceryl-4 isostearate (and) hexyl laurate (and) cetyl PEG/PPG-10/1 dimethicone | 3.5 |
| | Pigments | 9.9 |
| B1 | Cyclopentasiloxane | 16.1 |
| | Polysiloxane/polyamide PASi (MW: 14 × 10$^4$, DP 15) | 1.0 |
| | Silicone-acrylates | 12.0 |
| B2 | Polytrap/cyclopentasiloxane (filler) | 1.0 |
| | MMA Crosspolymer (filler) | 4.0 |
| | Nylon-12 (filler) | 1.0 |
| B3 | Preservatives | 0.4 |
| | Disteardimonium Hectorite (gelling agent) | 0.6 |
| | Propylene Carbonate | 0.2 |
| C | Water | 40.0 |
| | Magnesium sulfate | 1.0 |
| | Methylparaben (preservative) | 0.7 |
| | Non-ionic emulsifier | 0.5 |
| | Total | 100.0 |

This foundation is obtained in the following manner: heating of the silicone polyamide in the non-volatile oils until obtaining of a liquid mixture, addition of pigments, fillers, gelling agent, surfactants, then volatiles at 20° C. below the softening point of the polymer, addition of the aqueous phase, preservatives, and magnesium sulfate, then homogenization of the whole. The product obtained then is poured into a suitable container, of the foundation-case type.

The product obtained in this manner has, because of the incorporation into the liquid fatty phase of the combination of a polysiloxane (PS)/polyamide (PA) polymer and silicone acrylates, excellent non-transfer properties (demonstrated by the non-deposition of foundation on a small collar placed around the neck of made-up testers for several minutes). In addition, this foundation has the following properties: nonstickiness, flexibility, comfort, freshness. It makes possible a good application ("good application with cushion") and the deposit has an excellent resistance to water.

TABLE 10

Long-Wear Foundation Composition

| Phase | INCI Name | % |
|---|---|---|
| A | Ethylhexyl Methoxycinnamate | 4.0 |
|  | Cyclopentasiloxane (and) dimethicone copolyol | 8.0 |
|  | Cyclopentasiloxane (and) diphenyl dimethicone | 2.0 |
|  | Pigments | 9.9 |
| B | Cyclopentasiloxane | 18.0 |
|  | Polysiloxane/polyamide | 3.0 |
|  | Polyglyceryl-4-isostearate (and) hexyl laurate (and) cetyl PEG/PPG-10/1 dimethicone | 3.5 |
|  | Preservative | 0.2 |
| C | MMA crosspolymer (filler) | 4.5 |
|  | Polytrap in cyclopentasiloxane (filler) | 0.9 |
|  | Silica (filler) | 0.64 |
| D | Water | 32.16 |
|  | Butylene glycol (moisturizer) | 10.0 |
|  | Magnesium sulfate | 1.0 |
|  | Methylparaben (preservative) | 0.3 |
|  | Non-ionic emulsifier | 0.5 |
| E | Water | 1.0 |
|  | Preservative | 0.3 |
|  | TOTAL | 100.0 |

This foundation was obtained in the following manner. To begin, phase A is prepared by mixing the ingredients well and grinding them with a SILVERSON homogenizer at a speed of 6000 rpm. Separately, the phase B ingredients are heated to 80 to 85° C., with stirring for 10 to 15 minutes, or until dissolution of the polysiloxane/polyamide. Phases A and B then were combined in the main beaker and mixed well at the temperature of 60 to 65° C. Phase C was added to the main beaker and it is stirred until obtaining of a uniform mixture.

Phase D is heated to 65 to 70° C. in a separate side beaker. Emulsification is carried out by adding phase D to the main beaker with the aid of a homogenizer at medium/high speed. The product is cooled to 40 to 45° C., then phase E is added slowly with thorough stirring. The product is cooled to room temperature, by means of a paddle stirrer.

TABLE 11

Long-Wear Foundation Composition

| Phase | INCI Name | % |
|---|---|---|
| A | Ethylhexyl Methoxycinnamate | 4.0 |
|  | Cyclopentasiloxane (and) dimethicone copolyol | 8.0 |
|  | Cyclopentasiloxane (and) diphenyl dimethicone | 2.0 |
|  | Pigments | 9.9 |
| B | Cyclopentasiloxane | 18.0 |
|  | Polysiloxane/polyamide | 3.0 |
|  | Polyglyceryl-4-isostearate (and) hexyl laurate (and) cetyl PEG/PPG-10/1 dimethicone | 3.5 |
|  | Propylparaben | 0.2 |
| C | MMA crosspolymer | 4.5 |
|  | Polytrap/cyclopentasiloxane | 0.9 |
|  | Silica | 0.64 |
| D | Water | 42.16 |
|  | Magnesium sulfate | 1.0 |
|  | Preservative | 0.3 |
|  | Non-ionic emulsifier | 0.5 |
| E | Water | 1.0 |
|  | Preservative | 0.3 |
|  | TOTAL | 100.0 |

TABLE 12

Long-Wear Foundation Composition

| Phase | INCI Name | % |
|---|---|---|
| ACTIVE | MAGNESIUM SULFATE | 0.7 |
| CHARGE | SILICA | 1 |
| CHARGE | PERLITE | 0.2 |
| COLORANT | TITANIUM DIOXIDE (and) DISODIUM STEAROYL GLUTAMATE (and) ALUMINUM HYDROXIDE | 10.85 |
| COLORANT | IRON OXIDES (and) DISODIUM STEAROYL GLUTAMATE (and) ALUMINUM HYDROXIDE | 0.26 |
| COLORANT | IRON OXIDES (and) DISODIUM STEAROYL GLUTAMATE (and) ALUMINUM HYDROXIDE | 0.07 |
| COLORANT | IRON OXIDES (and) DISODIUM STEAROYL GLUTAMATE (and) ALUMINUM HYDROXIDE | 0.83 |
| CORPS GRAS | ISOHEXADECANE | 1.6 |
| FILTRE SOLAIRE | ETHYLHEXYL METHOXYCINNAMATE | 3 |
| POYLMERE | NYLON-12 | 3 |
| SILICONE | CYCLOHEXASILOXANE | 15.7 |
| SILICONE | CETYL PEG/PPG-10/1 DIMETHICONE | 1 |
| SILICONE | PEG-10 DIMETHICONE | 2 |
| SILICONE | ACRYLATES/POLYTRIMETHYLSILOXYMETHACRYLATE COPOLYMER | 10 |
| SOLVANT | BUTYLENE GLYCOL | 6 |
| SOLVANT | ALCOHOL DENAT. | 8 |
| SOLVANT | WATER | 34.79 |
| SOLVANT | ISODODECANE | 1 |

The foundations in Table 11 and 12 were obtained in a manner comparable to that described previously in Table 10.

The product obtained in this manner had, because of the incorporation into the fatty phase of a polysiloxane/polyamide polymer, excellent cosmetic properties, in particular of non-transfer and staying power, and properties of "comfortable wear, "nice application with cushion" and it is light during application—"feel light during application."

The product obtained in this manner had, because of the incorporation into the liquid phase of a polysiloxane/polyamide polymer (PASi), excellent cosmetic properties, in particular an easy, flowing application ("nice application with cushion"), a good resistance to transfer after drying, a very good resistance to water, a high level of comfort ("comfortable wear").

Example 6. Methods for Improving the Appearance of Skin

To improve the appearance of skin of a subject, the skin-tightening composition can be used as the followings:
(i) with the skin-tightening composition applied as a base coat and allowed to dry, wherein a skin-tightening film was formed on the skin. A long-wear cosmetic composition is consequently applied on top of the film; or
(ii) with a long-wear cosmetic composition applied to the skin as a base coat, followed by an optional drying period, and the skin-tightening composition applied on top so that a skin-tightening film formed on top of the long-wear cosmetic composition.

Example 7. Compatibility Between Skin-Tightening Composition and Long-Wear Foundation Test Objective: this study aimed to assess the efficacy of skin-tightening composition over long-wear foundation. The objective was to confirm skin-tightening composition usage with long-wear foundation (expert application in controlled condition).

Application Method: Expert application in a controlled environment. Half face application skin-tightening composition only versus skin-tightening composition over foundation. Ratings and images were taken at baseline, 10 minutes, 30 minutes, 3 hours, 6 hours, and after removal. Applied a moisturizer, then applied long-wear foundation of Table 12 over half face, then applied skin-tightening composition under eye area and under crow's feet on both sides. Skin-tightening composition application was performed using finger application.

Test Design: grade 4 Atlas score for under eye bags; crow's feet and wrinkles under eyes were different grades (evaluations and photos at application, 10 minutes, 30 minutes, 3 hours, 6 hours, and removal). This was in a controlled environment.

Figure 3:
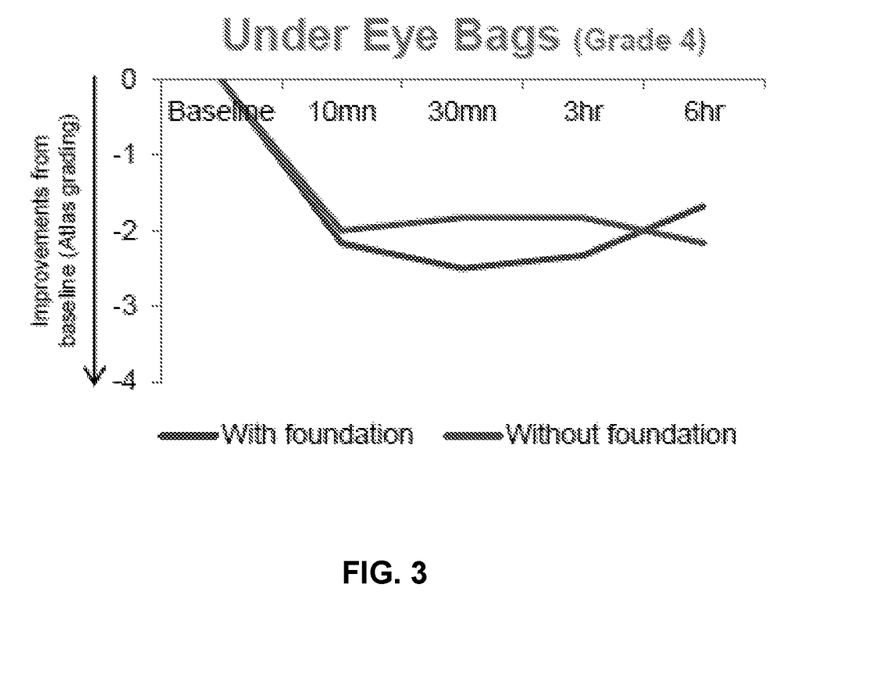
FIG. 3 shows skin-tightening composition compatibility with long-wear foundation under eye bag.

FIG. 3 shows skin-tightening composition (formula 6) compatibility with long-wear foundation under eye bag. The top curve shows the improvement from baseline without the long-wear foundation, and the bottom line shows the improvement from baseline with the long-wear foundation. The skin-tightening composition retained long lasting performance over foundation, and the long-wear foundation also showed good performance in terms of cracking, pigment migration, demarcation, and appropriate coverage.

We claim:

1. A system for improving the appearance of skin, comprising:
   (1) a skin tightening aqueous film forming composition comprising:
      a. from about 1% to about 20% by weight of a mixture of sodium silicate and pullulan;
      b. from about 0.3% to about 0.7% by weight of at least one polyvalent silicate thickener;
      c. from about 0.5% to about 15% by weight of acrylates copolymer;
      d. from about 2% to about 15% by weight of at least one plasticizer selected from the group consisting of glycerin, propylene glycol, butylene glycol, and propanediol;
      e. optionally, from about 0.1% to about 10% by weight of at least one cosmetic powder;
         wherein the composition provides a tightening sensation and smooths skin imperfections upon application to the skin and
   (2) a long-wear cosmetic composition comprising at least one silicone-polyamide copolymer, at least one silicone film former, and at least one volatile oil.

2. The system of claim 1, wherein the (a) mixture of sodium silicate and pullulan is present in an amount from 3% to 15% by weight of the total composition.

3. The system of claim 1, wherein the (b) at least one polyvalent silicate thickener is selected from the group consisting of magnesium silicate, calcium silicate, aluminum silicate, polyvalent silicate clays, montmorillonite, bentonite, smectite, and the mixtures thereof.

4. The system of claim 1, wherein the polyvalent silicate thickener(s) is present in an amount from 0.4% to 0.6% by weight of the total composition.

5. The system of claim 1, wherein the anionic associative polymeric thickener is present in an amount from 1% to 10% by weight of the total composition.

6. The system of claim 1, wherein the silicone-polyamide copolymer of the long-wear cosmetic composition is chosen from dimethicone copolymers and dimethicone crosspolymers.

7. The system of claim 1, wherein the silicone film former of the long-wear cosmetic composition is chosen from silsesquioxane, polyalkylsilsesquioxane, polymethylsilsesquioxane, siloxysilicate, trialkylsiloxysilicate, and trimethylsiloxysilicate.

8. The system of claim 1, wherein the volatile oil of the long-wear cosmetic composition is selected from the group consisting of volatile hydrocarbon-based oils, volatile silicone oils, and mixtures thereof.

9. The system of claim 1, wherein the long-wear cosmetic composition is a makeup composition, a foundation, or a concealer composition.

10. The system of claim 1, wherein the plasticizer(s) is/are present in an amount from 5% to 13% by weight of the total composition.

11. The system of claim 1, wherein the composition comprises (e) at least one cosmetic powder selected from the group consisting of talc, mica, magnesium carbonate, calcium carbonate, magnesium silicate, aluminum magnesium silicate, silica, titanium dioxide, zinc oxide, red iron oxide, yellow iron oxide, black iron oxide, polyethylene powder, methacrylate powder, polymethyl methacrylate, polystyrene powder, silk powder, crystalline cellulose, and mixtures thereof.

12. A method for improving the appearance of skin, said method comprising:
   (1) applying to the skin of a subject a long-wear cosmetic composition comprising at least one silicone-polyamide copolymer, at least one silicone film former, and at least one volatile oil; and, after an optional drying time;
   (2) forming a film on top of the long-wear cosmetic composition by applying a skin-tightening composition to the skin, the skin-tightening composition comprising:
      a. from about 1% to about 20% by weight of a mixture of sodium silicate and pullulan;
      b. from about 0.3% to about 0.7% by weight of at least one polyvalent silicate thickener;
      c. from about 0.5% to about 15% by weight of acrylates copolymer;
      d. from about 2% to about 15% by weight of at least one plasticizer selected from the group consisting of glycerin, propylene glycol, butylene glycol, and propanediol;
      e. optionally, from about 0.1% to about 10% by weight of at least one cosmetic powder.

13. A method for improving the appearance of skin, said method comprising:
   (1) forming a film on the skin by applying a skin-tightening composition to the skin, the skin-tightening composition comprising:
      a. from about 1% to about 20% by weight of a mixture of sodium silicate and pullulan;
      b. from about 0.3% to about 0.7% by weight of at least one polyvalent silicate thickener;
      c. from about 0.5% to about 15% by weight of acrylates copolymer;
      d. from about 2% to about 15% by weight of at least one plasticizer selected from the group consisting of glycerin, propylene glycol, butylene glycol, and propanediol;
      e. optionally, from about 0.1% to about 10% by weight of at least one cosmetic powder; wherein the composition provides a tightening sensation and smooths skin imperfections upon application to the skin;
   (2) applying to the skin on top of the film, a long-wear a cosmetic composition comprising at least one silicone-polyamide copolymer, at least one silicone film former, and at least one volatile oil.

* * * * *